United States Patent [19]

Marrese et al.

[11] Patent Number: 4,769,122

[45] Date of Patent: Sep. 6, 1988

[54] COMPACT ELECTROCHEMICAL CELL FOR GAS DETECTION

[75] Inventors: Carl A. Marrese, Gaithersburg, Md.; David J. D'Amico, Cheswick, Pa.; Peter M. Noble, Valencia, Pa.; Robert L. Novack, Evans City, Pa.; John H. Wolf, Monroeville, Pa.; Andrew A. Sicree, Dayton, Ohio

[73] Assignee: Bacharach, Inc., Pittsburgh, Pa.

[21] Appl. No.: 72,215

[22] Filed: Jul. 10, 1987

[51] Int. Cl.[4] .................. G01N 27/28; G01N 27/50
[52] U.S. Cl. ..................... 204/408; 204/412
[58] Field of Search ............... 204/412, 431, 432, 408

[56] References Cited

U.S. PATENT DOCUMENTS

| | | |
|---|---|---|
| Re. 31,914 | 6/1985 | Oswin et al. |
| Re. 31,915 | 6/1985 | Oswin et al. .................. 204/412 |
| Re. 31,916 | 6/1985 | Oswin et al. .................. 204/412 |
| 3,314,863 | 8/1963 | Hersch et al. .................. 204/1 |
| 3,449,231 | 6/1969 | Adams et al. .................. 204/415 |
| 3,577,332 | 5/1971 | Porter et al. .................. 204/408 |
| 3,622,487 | 11/1971 | Chand et al. .................. 204/195 |
| 3,755,125 | 8/1973 | Shaw et al. .................. 204/408 |
| 3,763,025 | 10/1973 | Chand .................. 204/1 T |
| 3,909,384 | 9/1975 | Jasinski et al. .................. 204/195 |
| 4,001,103 | 1/1977 | Blurton et al. .................. 204/195 |
| 4,025,412 | 5/1977 | LaConti .................. 204/195 R |
| 4,052,268 | 10/1977 | Blurton et al. .................. 204/1 T |
| 4,132,616 | 1/1979 | Tantram et al. .................. 204/195 P |
| 4,171,253 | 10/1979 | Nolan et al. .................. 204/195 S |
| 4,324,632 | 4/1982 | Tantram et al. .................. 204/195 P |
| 4,406,770 | 9/1983 | Chan et al. .................. 204/406 |
| 4,446,000 | 5/1984 | Cullinane, Jr. .................. 204/415 |
| 4,521,290 | 6/1985 | Venkatasetty .................. 204/412 |
| 4,587,003 | 5/1986 | Tantram et al. .................. 204/412 |
| 4,595,486 | 6/1986 | Schmidt et al. .................. 204/412 |
| 4,633,704 | 1/1987 | Tantram et al. .................. 73/23 |
| 4,662,996 | 5/1987 | Venkatasetty .................. 204/1 T |
| 4,666,565 | 5/1987 | Dobson .................. 204/1 T |

FOREIGN PATENT DOCUMENTS 2140566A 10/1984 United Kingdom ............... 204/1 T

OTHER PUBLICATIONS

CTL 3E CO Cell Drawing-Jan. 22, 1987.

Primary Examiner—G. L. Kaplan
Attorney, Agent, or Firm—Webb, Burden, Ziesenheim & Webb

[57] ABSTRACT

An electrochemical cell for use in gas detection includes a cell body having an electrolyte cavity and a separate sensor cavity. The sensor cavity holds stacked sensor elements including a counter electrode, electrolyte mat, reference electrode and sensing electrode. A wick draws the electrolyte from the electrolyte cavity to the electrolyte mat. The sensing electrode closes off the sensor cavity and seals the counter and reference electrodes therein. The only gas which contacts the counter and reference electrodes is that which passes through the sensing electrode or is generated by the counter electrode and becomes dissolved in the electrolyte.

35 Claims, 5 Drawing Sheets

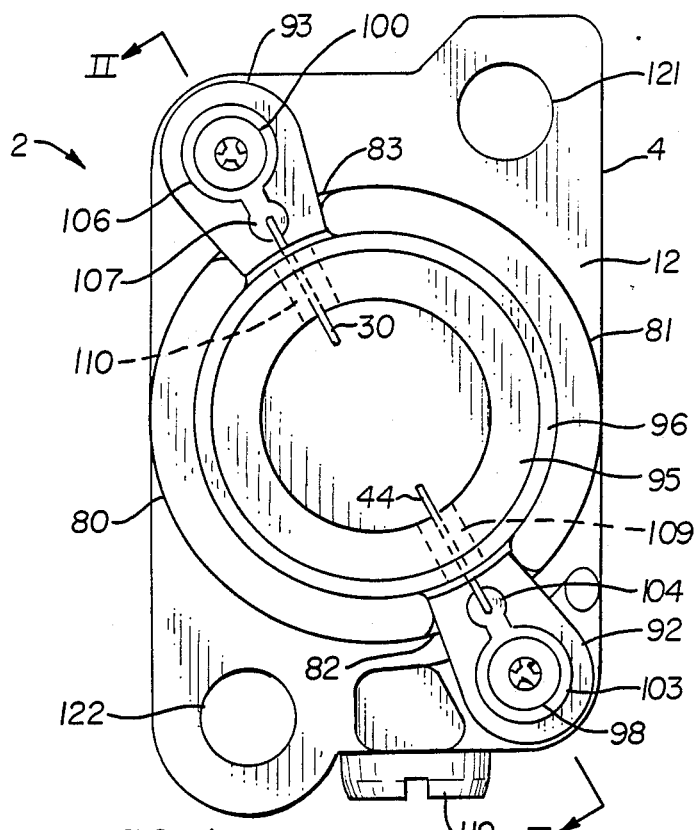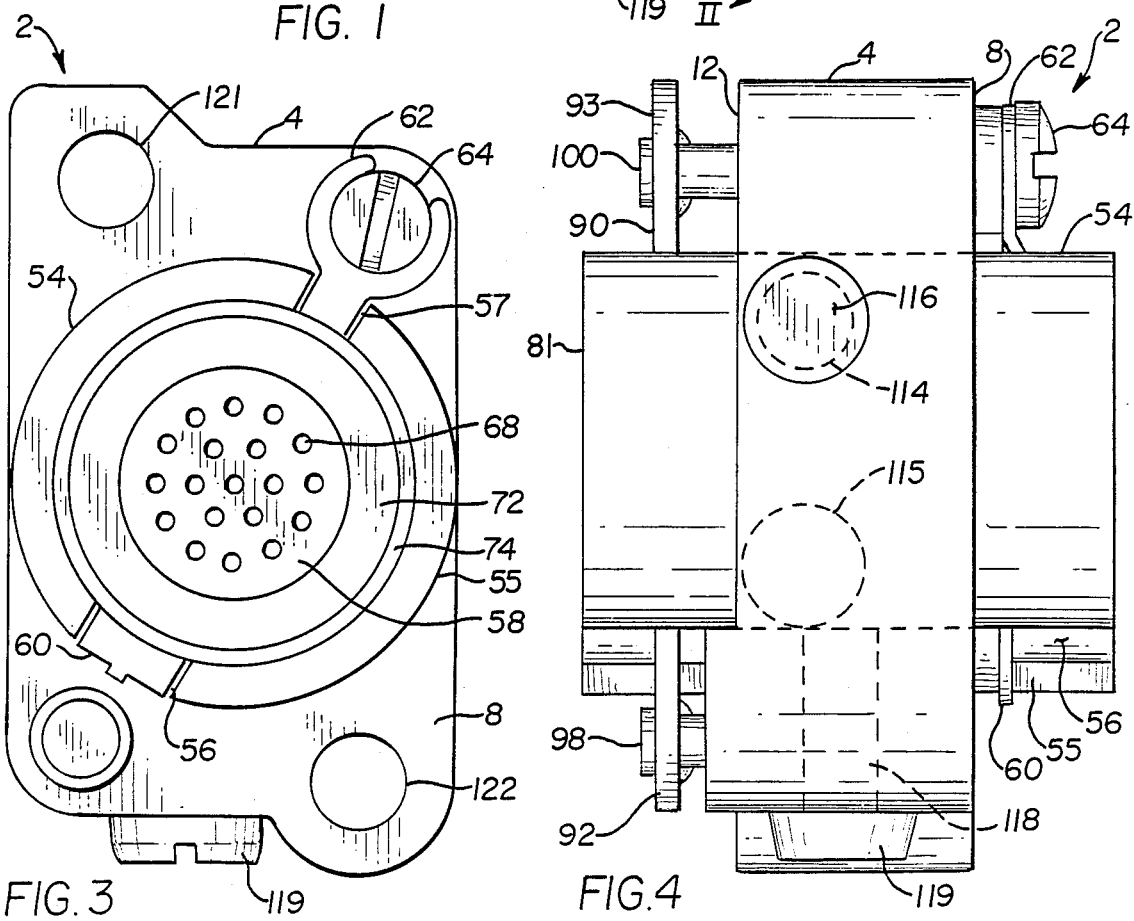

COMPACT ELECTROCHEMICAL CELL FOR GAS DETECTION

BACKGROUND OF THE INVENTION (1) Field of the Invention

This invention relates to electrochemical gas detectors and, more particularly, to a three electrode electromechanical cell having a compact design.

(2) Background Art

The theory and general operation of the three electrode electrochemical cells used in toxic or other gas detector systems are well known. Such cells include a sensing electrode, a counter electrode spaced from the sensing electrode, an aqueous-based electrolyte between and in contact with the sensing and counter electrodes, and a reference electrode positioned between the sensing and counter electrodes and in contact with the electrolyte. The sensing electrode is typically a porous, gas diffusion electrode having a coating of a catalytic material on a surface adjacent the electrolyte. The gas to be sensed, referred to as the object gas, flows either alone or in combination with other gases (e.g., the ambient atmosphere) through the sensing electrode. The object gas undergoes a reaction, either a reduction or an oxidation, at the interface of the electrolyte and the catalytic material of the sensing electrode. The catalytic material is selected to promote reaction with a particular object gas, but not to react with other gases that may accompany the object gas.

The sensing electrode will function electrochemically as an anode if the reaction occurring at the interface of the electrolyte and catalytic material is an oxidation, for example, if the cell is used to detect carbon monoxide, hydrogen, hydrogen sulfide, hydrocarbons, or other fuel gases that are readily oxidizable. In an oxidation reaction, electrons are removed from the molecules of the object gas. The sensing electrode will function electrochemically as a cathode if the reaction occurring at the interface of the electrolyte and catalytic material is a reduction, for example, if the cell is used to detect nitrogen dioxide, chlorine, fluorine, bromine, oxygen or other oxidant gases that are readily reducible. In a reduction reaction, electrons are added to the molecules of the object gas.

The result of either an oxidation or a reduction reaction at the sensing electrode is the production of charged particles in the form of ions. Charged particles will migrate through the electrolyte to the counter electrode. A conductive wire is typically connected external of the cell between the sensing and counter electrodes to complete an electrical path, to allow electrons to flow between the counter and sensing electrodes and to permit an opposite electrochemical reaction to take place at the counter electrode.

The reference electrode is used to maintain a particular potential difference between the sensing and reference electrodes and to assist or encourage the oxidation or reduction reaction at the sensing electrode. For example, in a carbon monoxide (CO) detecting cell, the sensing electrode is fixed at a potential that makes it run in an electron hungry mode in which CO, the object gas, will readily be oxidized and give up electrons. The reference electrode is also used to bias the sensing electrode at a particular level so that other reactions will not take place and, thereby, will not interfere with the desired reaction resulting from the presence of the object gas. The reference electrode potential will be sensed without drawing significant current and will not affect the magnitude of the current generated by the reaction of the object gas at the sensing electrode.

With all other conditions remaining constant, such as temperature, gas pressure, and humidity, the electrons generated by the reactions within the cell will be directly proportional to the amount of object gas contacting the sensing electrode. The current flowing through the external circuit between the sensing and counter electrodes can be measured by an ammeter or the like and give a quantitative reading of the level of object gas present.

Prior art three electrode cells useful for detecting an object gas in an atmosphere are shown, for example, in U.S. Pats. Nos. Re. 31,914; Re. 31,915; and Re. 31,916. However, these cells are rather bulky due to the positioning of the electrodes with respect to each other and with respect to an electrolyte reservoir in the cells since the electrodes are all exposed to atmospheric air.

It is, accordingly, an object of the present invention to provide a three electrode electrochemical cell for gas detection which has a compact design.

The prior art has attempted to provide a three electrode electrochemical cell of compact design, but these designs all have various disadvantages or unsatisfactory characteristics. U.S. Pat. No. 4,521,290 discloses a thin layer electrochemical cell for detecting toxic chemicals. However, this cell includes a plurality of counter electrodes which are spaced apart from the remainder of the cell and are located in an electrolyte reservoir. Such an arrangement does not permit the construction of a compact cell. The cell disclosed in United Kingdom Patent Application No. 2,140,566A includes a working or sensing electrode spaced from flat reference and counter electrodes by a powdered, semisolid electrolyte. These electrodes are each positioned on the outer surface of the electrolyte. This cell includes no reservoir of electrolyte and does not adjust at all for variations in humidity.

City Technology Limited, of London, England, markets a compact CO cell under Model Nos. 3ER and 3FR, and markets a compact $H_2S$ cell under Model No. 3HR. Similar cells are disclosed in U.S. Pats. Nos. 4,633,704, 4,587,003 and 4,406,770. These cells included porous, gas diffusion electrodes for the sensing, reference and counter electrodes and the electrodes are positioned in a stacked arrangement. However, these cells are not the most compact design available, utilize exclusively more expensive gas diffusion electrodes, weep liquid electrolyte after being used for a short time, and do not adequately compensate for variations in ambient humidity. In addition, the porous, hydrophobic reference and counter electrodes trap gas bubbles therein and, as a result, block off a portion of the catalytic material on the electrodes and interfere with the desired electrochemical reaction. Moreover, these cells provide a separate pathway between the counter electrode and the surrounding atmosphere.

It is a further object of the present invention to provide a compact, three electrode electrochemical cell which includes stacked electrodes, yet will operate efficiently, is inexpensive to manufacture, does not weep electrolyte, compensates readily for humidity changes and will operate in an ambient atmosphere having a high relative humidity.

SUMMARY OF THE INVENTION

Accordingly, we have invented an electrochemical cell for use in gas detection which includes an impervious, nonconductive cell body having an electrolyte cavity and a separate sensor cavity formed in the cell body. The electrolyte cavity is at least partially filled with a liquid electrolyte. The sensor cavity has a plurality of sensor elements stacked therein on top of each other. These sensor elements include a counter electrode positioned at an inner end of the sensor cavity and a gas diffusion sensing electrode positioned at an outer end of the sensor cavity and spaced from the counter electrode. An electrolyte mat is positioned between and contacts both the counter and the sensing electrodes. A reference electrode is disposed within the electrolyte mat and is spaced from the counter and sensing electrodes. The sensing electrode closes off the outer end of the sensor cavity and seals the counter electrode, reference electrode and electrolyte mat therein. The cell includes a wick for drawing liquid electrolyte from the electrolyte cavity to the electrolyte mat. The cell also includes means for making electrical contact with the counter, reference, and sensing electrodes. The reference electrode is formed of a non-porous, conductive material coated with a layer of a catalytic material. The counter electrode is a porous, hydrophilic conductive structure containing a catalytic material.

In the cell according to this invention, the counter and reference electrodes are totally submerged within the electrolyte and within the sensor cavity. Any gas which contacts the counter and reference electrodes comes solely from gas passing through the sensing electrode or generated at the counter electrode and becoming dissolved in the electrolyte.

This cell can be used for detecting oxidizable gases wherein the sensing electrode is an anode and the counter electrode is an oxygen reduction cathode, or for detecting reducible gases where the sensing electrode is a cathode. The counter electrode can be formed of an electrochemically inert metal coated with a layer of a catalytic material, such as a platinum screen coated with platinum black.

The electrolyte mat may include a top mat in contact with the sensing electrode and an adjacent bottom mat in contact with the counter electrode. The reference electrode is positioned between and in contact with the top and bottom mats. The bottom mat includes a stem, preferably integral therewith, which extends through the counter electrode and into the top and bottom mats and, thereby, in contact with the electrodes of the cell. The electrolyte cavity may be separated from the sensor cavity by a dividing wall and the stem may extend through a slot in the dividing wall. The bottom mat may be formed of first and second bottom mats, each of which include separate stems.

The cell may include a wire ring positioned behind and in contact with the counter electrode and terminating in a counter electrode lead wire which extends through the electrolyte cavity to a counter electrode connector. A carbon cloth may be positioned behind and in contact with both the counter electrode and the wire ring. The reference electrode may be a metal wire formed into one or more spaced loops and having a lead wire connected thereto. The reference electrode lead wire extends through the electrolyte mat, counter electrode and electrolyte cavity to a reference electrode connector. The counter electrode connector and reference electrode connector can be carried by a printed circuit board mounted to the cell body at an outer surface thereof.

The sensing electrode preferably includes a conductive outer surface and electrical contact with the sensing electrode may be made by a conductive ring positioned against the outer electrode and connected to a sensing electrode terminal at an outer portion of the cell. The electrical connection between the sensing electrode terminal and the conductive ring may be made by a planar sensor contact which has an enlarged central portion spaced from and covering the sensing electrode and having a plurality of holes therethrough to permit gas flow to the sensing electrode.

The cell may further include a diffusion barrier, such as a capillary tube or the like, through which the gas must flow to reach the sensing electrode. The cell body may include one or more vents extending into the electrolyte cavity, with the vents covered with a gas permeable and liquid impermeable membrane. A fill hole, closed by a removable plug, may extend through the cell body and into the electrolyte cavity.

A further understanding of the invention will be achieved from the following description taken with the accompanying drawings.

BRIEF DESCRIPTION OF THE DRAWINGS

In the drawings:

FIG. 1 is a back view of a first embodiment of an electrochemical cell in accordance with the present invention;

FIG. 3 is a front view of the electrochemical cell shown in FIG. 1;

FIG. 4 is a side view of the electrochemical cell shown in FIG. 1;

DETAILED DESCRIPTION OF THE DRAWINGS

Figure 2:
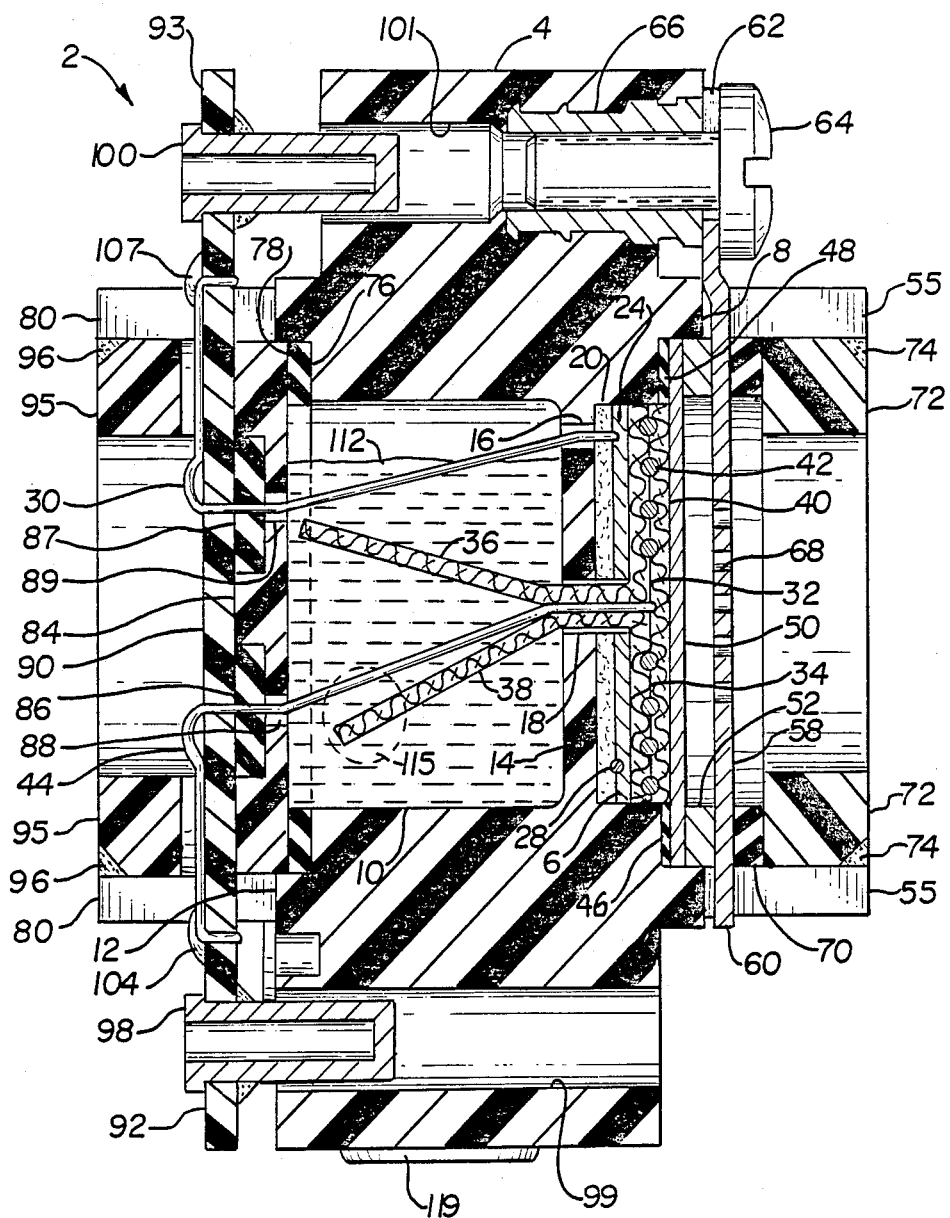
FIG. 2 is a section taken along lines II—II in FIG. 1.
Figure 5:
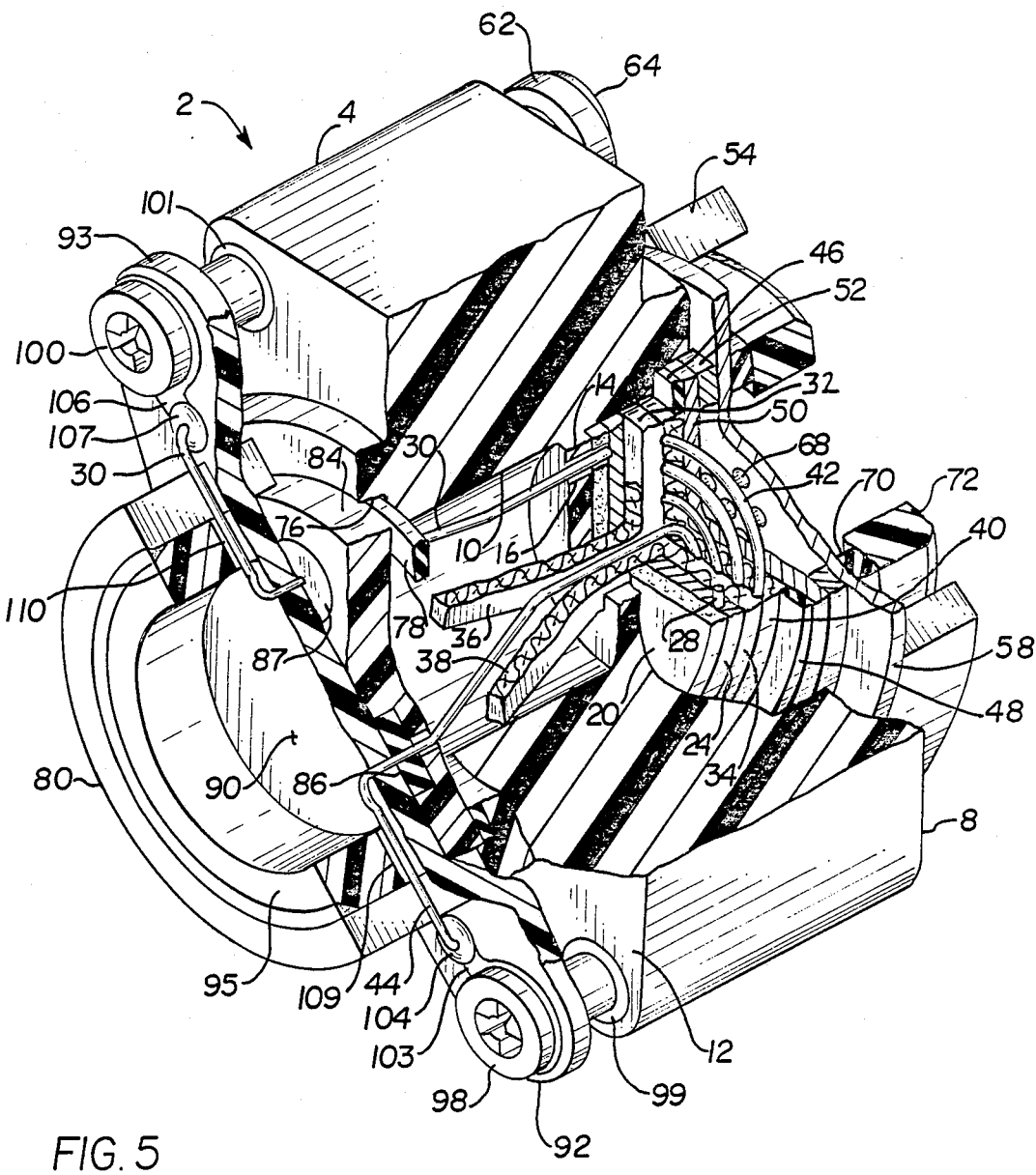
FIG. 5 is a perspective view, partially in section, of the electrochemical cell shown in FIG. 1.
Figure 6:
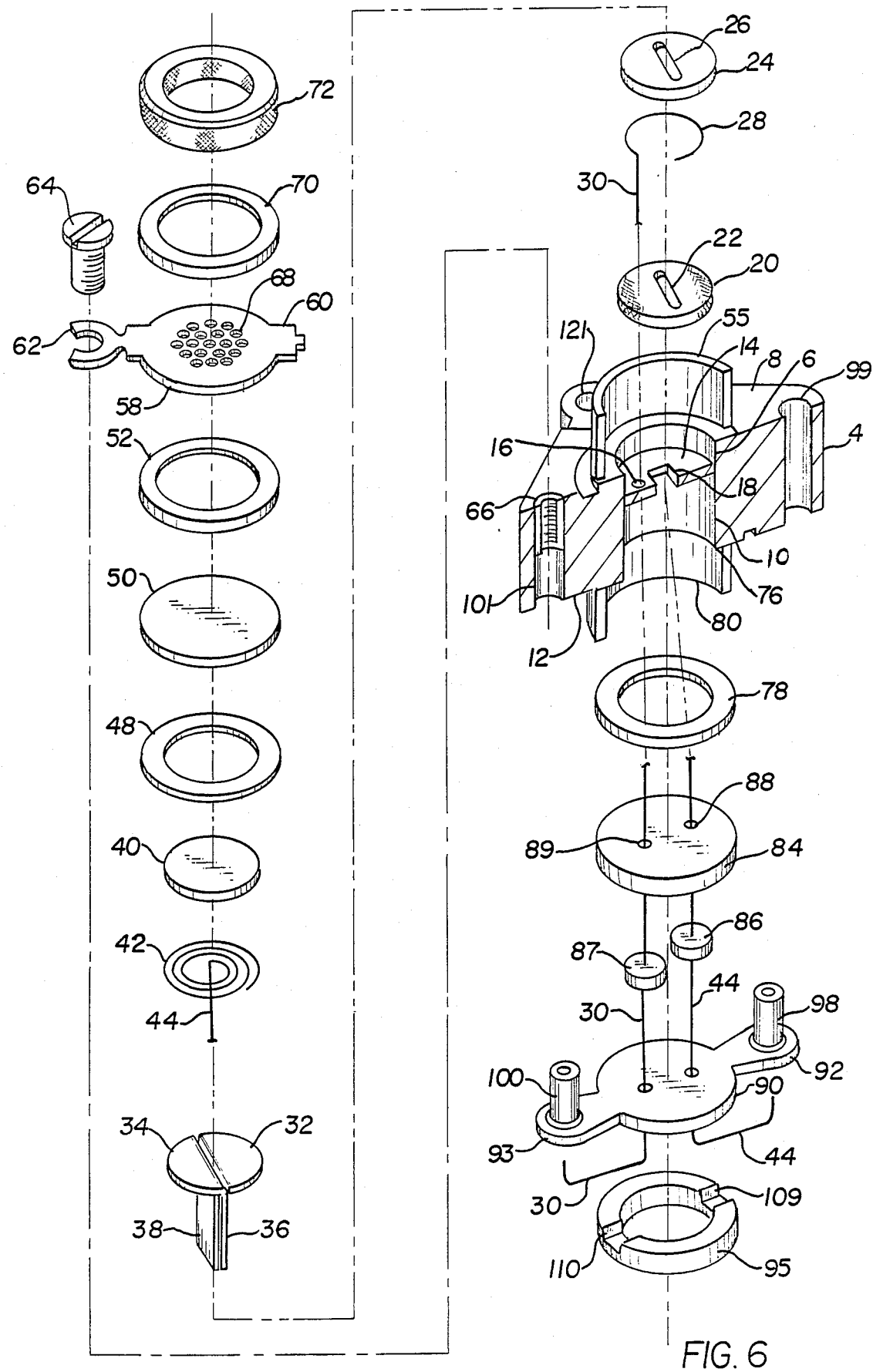
FIG. 6 is an exploded view, partially in section, of the electrochemical cell shown in FIG. 1.

Referring to FIGS. 1-6, there is shown a first embodiment of a three electrode, compact electrochemical cell 2 for toxic or other gas detection in accordance with the present invention. The cell 2 includes a generally parallelepiped shaped housing or cell body 4 which is formed of a relatively inert, non-conductive, gas impervious and acid resistant material such as high density polyethylene, polypropylene, polyimide, polyacrylate, polycarbonate or polyisocyanurate. A sensor cavity 6, preferably cylindrical in shape, extends into the cell body 4 from a front surface 8 thereof. An electrolyte cavity 10, similar in cross section to the sensor cavity 6, extends into the cell body 4 from a rear surface 12 thereof. The sensor cavity 6 and electrolyte cavity 10 are positioned in the approximate center of the front surface 8 and rear surface 12, respectively, of the cell body 4 and are substantially aligned with each other.

As will be explained hereinafter, the electrolyte cavity 10 has depth substantially greater than that of the sensor cavity 6. The sensor cavity 6 and electrolyte cavity 10 extend toward, but do not contact each other and are separated by a dividing wall 14. The dividing wall 14 is preferably integral with and formed of the same rigid material as the cell body 4. The dividing wall 14 has a wire hole 16 and a separate slot 18 extending therethrough between the sensor cavity 6 and the electrolyte cavity 10.

A thin, preferably planar, cylindrical carbon cloth layer or mat 20 is positioned within the sensor cavity 6 at an inner end thereof immediately adjacent the dividing wall 14. The carbon cloth layer 20 has a slot 22 extending therethrough which is aligned with and has the same general configuration as the slot 18 in the dividing wall 14. A thin, preferably planar, cylindrical counter electrode 24 is positioned within the sensor cavity 6 immediately adjacent the carbon cloth 20. The counter electrode 24 has a slot 26 extending therethrough which is aligned with and has the same general configuration as the slot 22 in the carbon cloth 20. A wire ring 28 is sandwiched between and is in electrical contact with the carbon cloth 20 and the counter electrode 24. The wire ring 28 makes electrical contact with a rear surface of the counter electrode 24. The carbon cloth 20 functions as a current collector and maintains electrical contact between the wire ring 28 and the counter electrode 24. The wire ring 28 terminates in a counter electrode lead wire 30 which extends through the carbon cloth 20, the wire hole 16 in the dividing wall 14, and the electrolyte cavity 10 to a rear portion of the cell 2. The wire ring 28 and counter electrode lead wire 30 may be formed as an integral unit from a length of thin platinum wire or the like.

A thin, preferably planar, cylindrical bottom electrolyte mat, formed of a semi-cylindrical first bottom mat 32 and a semi-cylindrical second bottom mat 34, is positioned within the sensor cavity 6 immediately adjacent the counter electrode 24 and on the surface of the counter electrode 24 opposite the carbon cloth 20 and wire ring 28. The first bottom mat 32 includes a first stem 36 integral therewith which extends in turn through slots 26, 22 and 18 in the counter electrode 24, carbon cloth 20 and dividing wall 14, respectively, and into the electrolyte cavity 10. Similarly, the second bottom mat 34 includes a second stem 38 integral therewith which is adjacent the first stem 36 and extends in turn through slots 26, 22 and 18 and into the electrolyte cavity 10. Stems 36 and 38 are substantially rectangular in configuration and have a width slightly smaller than the width of slots 18, 22 and 26. A thin, preferably planar, cylindrical top electrolyte mat 40 is positioned within the sensor cavity 6 immediately adjacent the bottom mat 32, 34 on the surface opposite the counter electrode 24. The bottom mat 32, 34 and top mat 40 are made of felt or a glass fiber filter type of material, such as fiberglass, capable of wicking a liquid from one location to another and holding the liquid therein.

A reference electrode 42 is sandwiched between and is in contact with the bottom mat 32, 34 and the top mat 40. The reference electrode 42 terminates in a reference electrode lead wire 44 which extends between the first stem 36 and second stem 38, and necessarily through slots 26, 22 and 18, and through the electrolyte cavity 10 to a rear portion of the cell 2. The reference electrode 42 is formed of a non-porous, conductive metal, such as an electrochemically inert metal, coated with a layer of catalytic material and has a plurality of openings or spaces through the structure. The reference electrode 42 and reference electrode lead wire 44 may be formed as an integral unit from a length of thin platinum wire or formed as a metal screen, with the reference electrode 42 coated with a layer of platinum black or other catalytic material. To increase the contact surface area, the reference electrode 42 is ideally formed in a spiral pattern with a plurality of outwardly extending and spaced coils. A metal mesh or screen structure could also be used. In this manner, the reference electrode 42 contacts the bottom mat 32, 34 and the top mat 40 but permits the majority of the surface area of the bottom mat 32, 34 and the top mat 40 to be in contact with each other.

The sensor cavity 6 flares outwardly to provide a wider portion at an outer end thereof at the front surface 8 of the cell 2 to form a front shoulder 46. A thin, ring-shaped rubber gasket 48 is positioned within the sensor cavity 6 adjacent the front shoulder 46 and surrounding the top mat 40. A sensing electrode 50, formed in the shape of a thin, planar, cylindrical disk, is positioned within the sensor cavity 6 adjacent to and in contact with both the top mat 40 and the gasket 48. A conductive ring 52 is positioned within the sensor cavity 6 adjacent to and in electrical contact with the sensing electrode 50.

The cell 2 includes a pair of opposed, semicircular walls 54, 55 extending outwardly therefrom and substantially surrounding the sensor cavity 6 at the front surface 8. Walls 54 and 55 are spaced apart from each other to form openings 56, 57 at adjacent ends. Openings 56 and 57 are diagonally opposed to each other.

A conductive sensor contact 58, in the shape of a thin, circular disk, is positioned within walls 54 and 55 and adjacent to and in electrical contact with the conductive ring 52. The sensor contact 58 includes a short tab 60 at one end and a contact terminal 62 diagonally opposite the short tab 60. When the sensor contact 58 is positioned on the cell 2, the short tab 60 extends between walls 54 and 55 in one of the openings, as shown through opening 56, and helps to keep the sensor contact 58 securely mounted thereto. The contact terminal 62 extends between walls 54 and 55 in the other opening, as shown through opening 57, and surrounds and is in electrical contact with a sensor electrode connector screw 64. Screw 64 passes through the contact terminal 62 and into a threaded connector 66 embedded in the cell body 4. One or more openings or holes 68 extend through the central or disk shaped portion of the sensor contact 62. The central portion of the sensor contact 62 is spaced away from the sensing electrode 50 by the thickness of the conductive ring 52. The sensor contact 62 provides an external electrical connection to the sensing electrode 50 and protects the fragile sensing electrode 50 from being physically contacted, except by a gas, and possibly damaged.

A ring-shaped, rubber cushion gasket 70 is positioned within the walls 54, 55 and adjacent the sensor contact 58. A first ring plug 72 is positioned within the walls 54, 55 and adjacent the cushion gasket 70. The first ring plug 72 may be securely affixed to the interior of walls 54, 55 by adhesive 74 or the like. In this manner, all of the previously discussed elements which are stacked both within and above the sensor cavity 6 will be maintained securely in place and in contact with the elements immediately adjacent thereto.

The electrolyte cavity 10 in the cell body 4 flares outwardly in a wider portion at the rear surface 12 of the cell 2 to form a rear shoulder 76. A ring-shaped rubber gasket 78 is positioned within the electrolyte cavity 10 adjacent the rear shoulder 76. The cell 2 includes a pair of opposed, semicircular walls 80, 81 extending outwardly therefrom and substantially surrounding the electrolyte cavity 10 at the rear surface 12. Walls 80 and 81 are spaced apart from each other to form openings 82, 83 at adjacent ends. Openings 82 and 83 are diagonally opposed to each other.

A circular septum disk 84 is positioned within and in contact with walls 80, 81 and in contact with gasket 78. A pair of disk-shaped rubber cell septums 86, 87 extend partially into the septum disk 84 in corresponding depressions and are substantially flush with an outer surface of the septum disk 84. A hole 88 extends through the septum disk 84 from a rear surface adjacent the electrolyte cavity 10 to the depression holding cell septum 86. Likewise, a hole 89 extends through the septum disk 84 to the depression holding cell septum 87.

A printed circuit board 90 is positioned within walls 80, 81 and adjacent the septum disk 84 and cell septums 86, 87. The printed circuit board 90 is formed in the shape of a flat, circular disk having ears 92, 93 extending outwardly therefrom and diagonally opposed to each other. The central disk portion of the printed circuit board 90 is located within walls 80, 81 and the ears 92, 93 extend through the openings between walls 80 and 81. As shown, ear 92 extends through opening 82 and ear 93 extends through opening 83. A second ring plug 95 is positioned within walls 80, 81 and adjacent the printed circuit board 90. The second ring plug 95 may be securely affixed to the interior of walls 80, 81 by adhesive 96 or the like. In this manner, all of the previously discussed elements which are stacked both within and above the electrolyte cavity 10 will be maintained securely in place and in contact with the elements immediately adjacent thereto.

Each ear 92, 93 on the printed circuit board 90 carries a plug receiving electrical connector. Ear 92 carries a reference electrode connector 98 which extends into a hole 99 in the cell body 4 beneath ear 92. Likewise, ear 93 carries a counter electrode connector 100 which extends into a hole 101 in the cell body beneath ear 93. The reference electrode lead wire 44 extends, in turn, through the electrolyte cavity 10, hole 88, cell septum 86, and the printed circuit board 90. Lead wire 44 then extends along the outer surface of the printed circuit board 90 beneath the second ring plug 95 and is connected to electrical trace 103 on ear 92 by solder 104 or the like. Electrical trace 103 extends on the outer surface of the printed circuit board 90 around and in electrical contact with the reference electrode connector 98. In this manner an electrical path is formed from the reference electrode 42 at the interior of the cell 2 along lead wire 44 to the reference electrode connector 98 at the exterior of the cell 2. The free end of lead wire 44 may be turned back into the printed circuit board 90 as shown, before solder 104 is applied, to form a more secure connection.

Similarly, the wire ring lead wire 30 extends, in turn, through the electrolyte cavity 10, hole 89, cell septum 87, and the printed circuit board 90. Lead wire 30 then extends along the outer surface of the printed circuit board 90, beneath the second ring plug 95 and is connected to electrical trace 106 on ear 93 by solder 107 or the like. Electrical trace 106 extends on the outer surface of the printed circuit board 90 around and in electrical contact with the counter electrode connector 100. The free end of lead wire 30 may also be turned back into the printed circuit board 90 before solder 107 is applied. An electrical path is formed from the counter electrode 24 located within the cell 2, through wire ring 28 and lead wire 30 to the counter electrode connector 100 at the exterior of the cell 2. The second ring plug 95 may include passageways 109, 110 along a bottom surface thereof and aligned with openings 82, 83 to accommodate lead wires 44 and 30, respectively, passing therebeneath.

The electrolyte cavity 10 is closed off at the rear surface 12 of the cell 2 by the septum disk 84 and is partially filled with a liquid electrolyte 112 such as sulfuric acid, phosphoric acid or any other known ionic acid electrolyte. The gasket 78 at the rear shoulder 76 and the cell septums 86, 87 surrounding lead wires 44 and 30, respectively, prevent the liquid electrolyte 112 from leaking out of the cell 2. The first stem 36 and second stem 38 are positioned within the liquid electrolyte 112 and function to draw or wick the electrolyte 112 to the first bottom mat 32 and second bottom mat 34. The liquid electrolyte 112 will travel from the bottom mat 32, 34 to the top mat 40. In this manner, the counter electrode 24, reference electrode 42 and sensing electrode 50 will always be in contact with the liquid electrolyte 112 and will be continuously wetted thereby.

A first vent hole 114 extends through the cell body 4 from one side and into the electrolyte cavity 10. Similarly, a second vent hole 115 extends through the cell body 4 from the opposite side and into the electrolyte cavity 10. The vent holes 114, 115 are covered at the exterior of the cell 2 by a membrane 116 which is permeable to gas, yet impermeable to liquid. The membrane 116 covered vent holes 114, 115 allows gas to enter and exit the electrolyte cavity 10 due to swelling or contracting of the liquid electrolyte 112. Generally, the liquid electrolyte 112 will swell when exposed to humid air, since the electrolyte 112 is hydrophilic. The vent holes 114, 115 provide a means to compensate for volumetric changes in the electrolyte 112. The vent holes 114, 115 are preferably aligned diagonally opposed to each other so that one vent hole remains uncovered by the electrolyte 112 regardless of the orientation of the cell 2. A preferred membrane 116 for covering the vent holes 114, 115 is a thin, Gore-Tex TM membrane. A fill hole 118 extends through the cell body 4 from one side and into the electrolyte cavity 10 and is used to add electrolyte 112 thereto as needed. Fill hole 118 may be closed by screw 119 or the like after the electrolyte 112 has been added.

The cell 2 may include one or more mounting holes therethrough. The cell 2 includes mounting holes 121 and 122 extending through the cell body 4 between the front surface 8 and the rear surface 12 at diagonally opposed corners. The cell 2 may be electrically connected to a control circuit of a gas detector by means of the sensor electrode screw 64, the reference electrode connector 98 and the counter electrode connector 100.

The sensing electrode 50 is a gas diffusion electrode which allows gas to pass therethrough but will not permit the liquid electrode 112 to pass. Such electrodes either include a catalytic material on a porous, conductive substrate or are formed of a porous, conductive catalytic material. The catalytic material of the sensing electrode 50 is oriented against the top mat 40 and is in contact with the electrolyte 112 contained therein. The sensing electrode 50 may be any of the known gas diffusion electrodes which have been used in gas sensors. For example, an anodic sensing electrode useful in detecting CO is platinum or platinum black on a carbon substrate. An anodic sensing electrode useful in detecting $H_2S$ is gold or gold oxide on a carbon substate. A cathodic sensing electrode useful in detecting $NO_2$ or halogens is a porous carbon substrate. In forming, for example, the platinum/carbon sensing electrode, a mixture of platinum and carbon or graphite can be placed on a PTFE or Teflon TM tape to form the gas diffusion electrode. Alternatively, a mixture of platinum, carbon and PTFE particles can be sintered together or platinum particles can be pressed into a carbon paper or cloth. A cathodic sensing electrode could be formed in the same manner by eliminating the platinum particles.

The counter electrode 24 is a porous, hydrophilic conductive structure filled or coated with a catalytic material. It may be a pressed, porous carbon layer with a platinum coating. The counter electrode 24 may also be an electrochemically inert metal screen coated with a catalytic material, such as a tantalum or niobium screen coated with platinum. In general, the counter electrode 24 need not be a gas diffusion electrode. As with the sensing electrode 50, the catalytic material of the counter electrode 24 must be in contact with the electrolyte 112.

The electrochemical cell 2 of the present invention arranges the counter electrode 24, reference electrode 42 and sensing electrode 50 in a stacked manner and located within a sealed sensor cavity 6 in the cell 2. Only the outer surface of the sensing electrode 50 is exposed to the surrounding atmosphere. The counter electrode 24 and reference electrode 42 are totally encased or submerged within the cell 2 and have no direct contact with the surrounding gaseous atmosphere. The only gas which comes in contact with the counter electrode 24 or reference electrode 42 is that gas which either passes through the sensing electrode 50 or is generated by the counter electrode 24 and becomes dissolved in the electrolyte in the bottom mat 32, 34 and top mat 40. By closely spacing the sensing electrode 50 and counter electrode 24, the gas dissolved in the electrolyte 112 is sufficient for the operation of the counter electrode 24 and reference electrode 42.

In addition, the electrolyte 112 contained in the electrolyte cavity 10 is totally separate from the cell electrodes. The electrolyte 112 needed for cell operation is wicked or drawn from the electrolyte cavity 10 by means of the first stem 36 and second stem 38 and placed in contact with the electrodes by the bottom mats 32, 34 and the top mat. Additional electrolyte 112 is drawn up to the electrodes as needed. Since the electrodes and electrolyte mats are relatively thin members, the sensor cavity 6 need not be as deep as the electrolyte cavity 10. Therefore, the electrolyte cavity 10 can be relatively large, and hold a larger reserve of electrolyte 112 for long term operations of the cell 2, without compromising the compact design of the cell. Moreover, by placing the counter electrode 24 close to the sensing electrode 50, only a small volume of electrolyte 112 is needed therebetween and the internal impedance of the cell is decreased.

In a preferred embodiment, the electrolyte cavity 10 will have a capacity on the order of 1 milliliter, the counter electrode 24 will be spaced from the sensing electrode by 0.040' or less, and the volume of electrolyte therebetween is about 120 $\mu$l.

In operation, a mixture of the object gas and the surrounding atmospheric gas passes through the holes 68 in the sensor contact 58 and fills the volume between the sensor contact 58 and the sensing electrode 50. The gas mixture will diffuse through the sensing electrode 50 and the object gas will undergo a reaction (either reduction or oxidation) at the interface of the electrolyte and catalytic material and generate charged particles. The object gas will be totally consumed during this process. The counter electrode 24 and reference electrode 42 need oxygen or other fuel gases to function correctly. The atmospheric gas passing through the sensing electrode 50 is dissolved in the electrolyte 112 and passes through the top mat 40 and bottom mat 32, 34 to the counter electrode 24 and reference electrode 42. For example, in a CO or $H_2S$ sensor, the counter electrode needs oxygen to function and this source of oxygen is derived solely from the atmospheric gas dissolved in the electrolyte. The object gas does not contaminate the gas dissolved in the electrolyte 112 since it was consumed during the reaction at the sensing electrode 50. The gas dissolved in the electrolyte 112 is sufficient to operate the cell 2 due to the close proximity of the counter electrode 24 to the sensing electrode 50.

Figure 7:
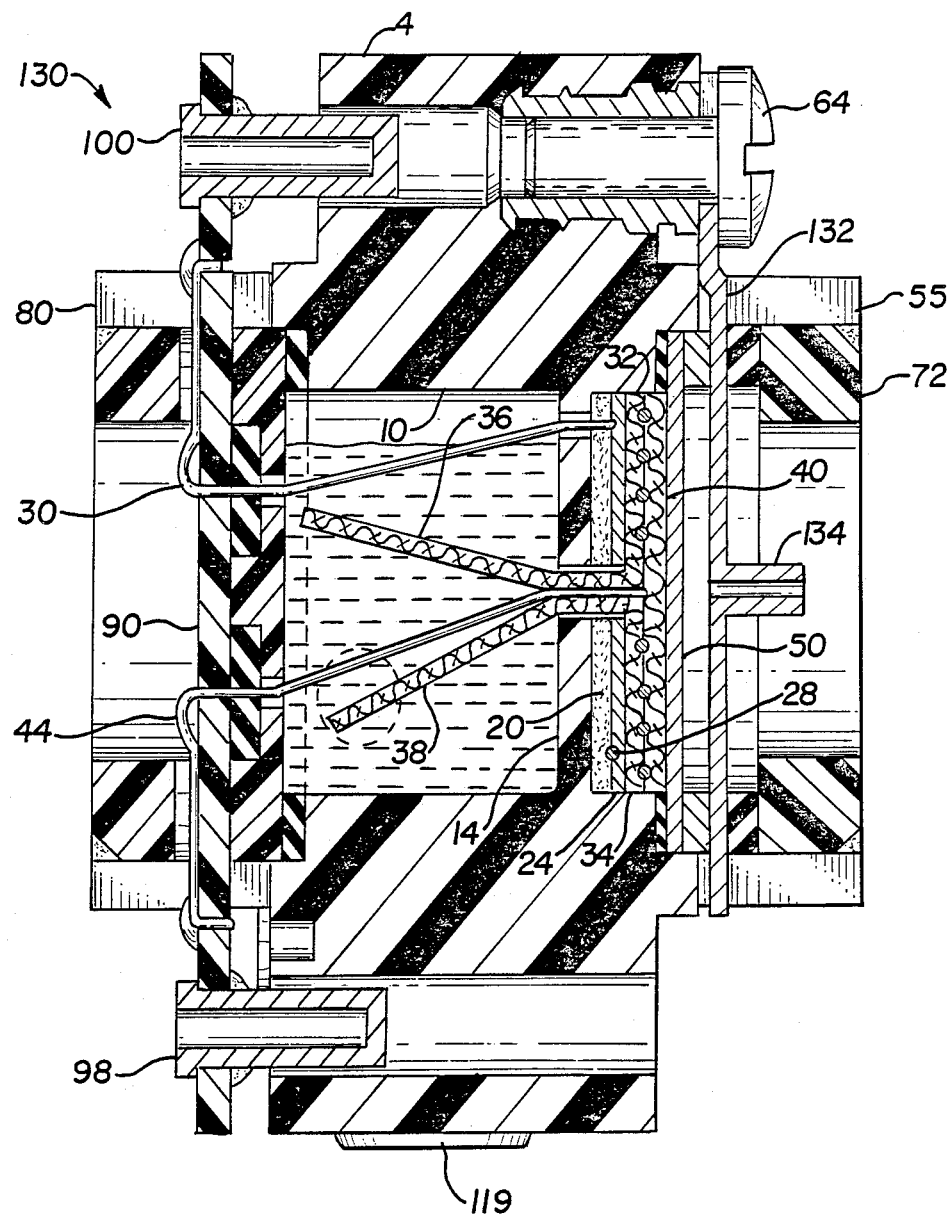
FIG. 7 is a section taken through a second embodiment of an electrochemical cell in accordance with the present invention.

A second embodiment of a three electrode, electrochemical cell 130 in accordance with the present invention is shown in FIG. 7. Cell 130 is identical to cell 2 shown in FIGS. 1-6, except for the sensor contact, and, therefore, identical elements will be identified by identical reference numbers. In the cell 130 shown in FIG. 7, sensor contact 132 is a solid disk (with no plurality of holes 68 therethrough) and includes a diffusion barrier 134 to restrict the flow of gas to the sensing electrode 50. The diffusion barrier utilized may be any of the known diffusion barriers, such as capillaries, membranes, porous plugs, and the like. Known diffusion barriers are shown, for example, in U.S. Pat. Nos. 4,446,000, 4,324,632 and 4,132,616, and disclosures of which are incorporated herein by reference. The diffusion barrier 134 shown in FIG. 7 is a capillary tube, although other barriers could be used in place of or in combination with a capillary tube.

The present invention is further described in the following Examples.

EXAMPLE I

A carbon monoxide electrochemical gas cell in accordance with the present invention was built and tested. The housing was formed of General Electric Ultem TM polyimide plastic material. The sensing electrode was a gas diffusion electrode formed of a mixture of 10% platinum on vulcan carbon utilizing 33 to 50% Teflon TM particles pressure bonded to a Prototech PC-206 carbon board. The Teflon TM particles increased the flexibility and the hydrophobicity of the electrode and maintained a path for gas permeation through the electrode and into the electrolyte. The counter electrode was made of 10% platinum on vulcan carbon formed into a self-supporting layer with 33% Teflon TM particles. The counter electrode was active on both sides, resulting in a higher electrode area for oxygen reduction but with a thin electrode. The reference electrode was a platinized platinum wire coil and the electrolyte mats were formed of a glass fiber filter material. The reference electrode was spaced 0.015" from the counter electrode (the thickness of the bottom mat) and the counter and sensing electrodes were separated by 0.038". The electrolyte was 2.5N sulfuric acid and the electrolyte cavity had a capacity of about 750 $\mu$l.

The cell was tested on a standard circuit having a 10 ohm load resistor. The operating potentials between the sensing electrode and the counter electrode and between the counter electrode and reference electrode were each maintained at about 38 mv. The operating potential between the sensing electrode and reference electrode was about 0.2 mv. The output signal sensitivity taken across the load resistor was found to be approximately 0.05 to 0.21 $\mu$A per parts per million (ppm) of carbon monoxide.

EXAMPLE II

A nitrogen dioxide electrochemical gas cell in accordance with the present invention was built and tested. This cell was similar to the cell described in Example I except that the sensing electrode included no platinum particles and the electrolyte was a 20% phosphoric acid solution.

The cell was operated in a reducing mode by a standard test circuit. A varying potential was applied across the sensing and counter electrodes. It was determined that the cell gave an optimal current response in the range of $-70$ to $-100$ mv with respect to the reference electrode when exposed to 1164 ppm nitrogen dioxide at 1.0 liter/min flow rate. A typical maximum cell response current for 1164 ppm nitrogen dioxide was approximately $-600$ $\mu$A when the cell was operated at a voltage of $-75$ mv with respect to the reference electrode.

The average cell response time (90% of maximum signal) was 27 seconds for the 1164 ppm concentration and the average cell recovery time (drop to 10% of maximum signal) was 20 seconds. The cell signal response versus $NO_2$ concentration was linear, with a slope of 0.46 $\mu$A per ppm $NO_2$, in the range of 10 to 1200 ppm and showed that the cell could operate as a reliable $NO_2$ sensor in that range.

Having described herein the presently preferred embodiments of the present invention, it is to be understood that the invention may be otherwise embodied within the scope of the appended claims.

We claim:

1. An electrochemical cell for gas detection comprising an impervious nonconductive cell body having an electrolyte cavity and a separate sensor cavity formed therein, said electrolyte cavity being at least partially filled with a liquid electrolyte, said sensor cavity having a plurality of sensor elements stacked therein including a counter electrode positioned at an inner end of said sensor cavity, a gas diffusion sensing electrode containing a catalytic material and positioned at an outer end of said sensor cavity and spaced from said counter electrode, an electrolyte mat positioned between and contacting said counter and sensing electrodes, and a reference electrode disposed within said electrolyte mat and spaced from said counter and sensing electrodes, said reference electrode formed of a non-porous, conductive material coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off the outer end of said sensor cavity and sealing said counter electrode, reference electrode and electrolyte mat within said sensor cavity, said cell including wick means for wicking liquid electrolyte from said electrolyte cavity to said electrolyte mat, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte.

2. The electrochemical cell of claim 1 wherein said sensing electrode includes a catalytic material which will reduce a particular gas in contact therewith.

3. The electrochemical cell of claim 1 wherein said sensing electrode includes a catalytic material which will oxidize a particular gas in contact therewith.

4. The electrochemical cell of claim 1 wherein said counter electrode is formed of an electrochemically non-reactive metal coated with a layer of a catalytic material.

5. The electrochemical cell of claim 1 wherein said electrolyte mat includes a top mat in contact with said sensing electrode and an adjacent bottom mat in contact with said counter electrode and with said top mat, with the reference electrode positioned between and in contact with said top mat and said bottom mat.

6. The electrochemical cell of claim 5 wherein said wick means is a stem extending through said counter electrode and between the electrolyte in said electrolyte cavity and said bottom mat.

7. The electrochemical cell of claim 6 wherein said electrolyte cavity is separated from said sensor cavity by a dividing wall and said stem extends through a slot in said dividing wall.

8. The electrochemical cell of claim 7 wherein said bottom mat is formed of a first bottom mat and an adjacent second bottom mat, and wherein said stem includes a first stem integral with said first bottom mat and a second stem integral with said second bottom mat.

9. The electrochemical cell of claim 6 wherein said top mat, bottom mat and stem are formed of a glass fiber material.

10. The electrochemical cell of claim 1 wherein said sensing electrode has a conductive outer surface and said cell further includes a conductive ring in contact with the outer surface of said sensing electrode and electrically connected to a sensing electrode terminal at an outer portion of said cell.

11. The electrochemical cell of claim 1 further including a diffusion barrier through which gas must flow to reach the sensing electrode.

12. The electrochemical cell of claim 11 wherein said diffusion barrier is a capillary tube.

13. The electrochemical cell of claim 1 wherein said cell body has one or more vents extending into said electrolyte cavity, with said vents covered by a gas permeable and liquid impermeable membrane.

14. The electrochemical cell of claim 1 wherein said cell body has a fill hole extending into said electrolyte cavity, with said fill hole closed by a removable plug.

15. An electrochemical cell for gas detection comprising an impervious, nonconductive cell body having an electrolyte cavity extending into said cell body from a rear surface thereof and a sensor cavity extending into said cell body from a front surface thereof, a dividing wall separating said sensor cavity and electrolyte cavity, means for closing off said electrolyte cavity at said rear surface, said electrolyte cavity being at least partially filled with a liquid electrolyte, said sensor cavity having a counter electrode at an inner end thereof and adjacent said dividing wall, an electrolyte mat adjacent said counter electrode, a gas diffusion sensing electrode containing a catalytic material and positioned adjacent said electrolyte mat and spaced from said counter electrode, a reference electrode disposed within said electrolyte mat and spaced from said counter and sensing electrodes, with said reference electrode formed of a non-porous, conductive material coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off said sensor cavity at said front surface and sealing said counter electrode, reference electrode and electrolyte mat therein, said cell including a wick which extends between said electrolyte mat and the electrolyte in said electrolyte cavity and passes through said counter electrode and dividing wall, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte.

16. The electrochemical cell of claim 15 wherein said sensing electrode includes a catalytic material which will reduce a particular gas in contact therewith.

17. The electrochemical cell of claim 15 wherein said sensing electrode includes a catalytic material which will oxidize a particular gas in contact therewith.

18. The electrochemical cell of claim 15 wherein said counter electrode is formed of an electrochemically non-reactive metal coated with a layer of a catalytic material.

19. The electrochemical cell of claim 15 wherein said sensing electrode has a conductive outer surface and said cell further includes a conductive ring in contact with the outer surface of said sensing electrode and electrically connected to a sensing electrode terminal at a front portion of said cell.

20. The electrochemical cell of claim 15 further including a diffusion barrier through which gas must flow to reach the sensing electrode.

21. An electrochemical cell for gas detection comprising an impervious nonconductive cell body having an electrolyte cavity and a separate sensor cavity formed therein, said electrolyte cavity being at least partially filled with a liquid electrolyte, said sensor cavity having a plurality of sensor elements stacked therein including a counter electrode positioned at an inner end of said sensor cavity, a gas diffusion sensing electrode containing a catalytic material and positioned at an outer end of said sensor cavity and spaced from said counter electrode, an electrolyte mat positioned between and contacting said counter and sensing electrodes, and a reference electrode disposed within said electrolyte mat and spaced from said counter and sensing electrodes, said reference electrode formed of a non-porous, conductive material coated with a layer of catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off the outer end of said sensor cavity and sealing said counter electrode, reference electrode- and electrolyte mat within said sensor cavity, said cell including wick means for wicking liquid electrolyte from said electrolyte cavity to said electrolyte mat, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte, and further including a wire ring positioned behind and in contact with said counter electrode and terminating in a counter electrode lead wire which extends through said cell body and through said electrolyte cavity to a counter electrode connector at an outer portion of said cell and forms the means for making electrical contact with said counter electrode.

22. The electrochemical cell of claim 21 wherein said wire ring is formed of platinum.

23. The electrochemical cell of claim 21 further including a carbon cloth positioned behind and in contact with said counter electrode and said wire ring.

24. An electrochemical cell for gas detection comprising an impervious nonconductive cell body having an electrolyte cavity and a separate sensor cavity formed therein, said electrolyte cavity being at least partially filled with a liquid electrolyte, said sensor cavity having a plurality of sensor elements stacked therein including a counter electrode positioned at an inner end of said sensor cavity, a gas diffusion sensing electrode containing a catalytic material and positioned at an outer end of said sensor cavity and spaced from said counter electrode, an electrolyte mat positioned between and contacting said counter and sensing electrodes, and a reference electrode disposed within said electrolyte mat and spaced from said counter and sensing electrodes, with said reference electrode being a metal wire formed into one or more spaced loops and coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off the outer end of said sensor cavity and sealing said counter electrode, reference electrode and electrolyte mat within said sensor cavity, said cell including wick means for wicking liquid electrolyte from said electrolyte cavity to said electrolyte mat, and including means for making electrical contact with said counter, reference and sensing electrodes, wherein said counter and reference electrodes are submerged within said sensor cavity by said sensing electrode and any gas contacting said counter and reference electrode passes through said sensing electrode and is dissolved in said electrolyte.

25. The electrochemical cell of claim 24 wherein said reference electrode is a platinum wire formed into a plurality of spaced loops and coated with a layer of platinum black.

26. An electrochemical cell for gas detection comprising an impervious nonconductive cell body having an electrolyte cavity and a separate sensor cavity formed therein, said electrolyte cavity being at least partially filled with a liquid electrolyte, said sensor cavity having a plurality of sensor elements stacked therein including a counter electrode positioned at an inner end of said sensor cavity, a gas diffusion sensing electrode containing a catalytic material and positioned at an outer end of said sensor cavity and spaced from said counter electrode, an electrolyte mat positioned between and contacting said counter and sensing electrodes, and a reference electrode disposed within said electrolyte mat and spaced from said counter and sensing electrodes, said reference electrode formed of a non-porous, conductive material coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off the outer end of said sensor cavity and sealing said counter electrode, reference electrode and electrolyte mat within said sensor cavity, said cell including wick means for wicking liquid electrolyte from said electrolyte cavity to said electrolyte mat, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte, and further including a reference electrode lead wire connected to said reference electrode and which extends through said electrolyte mat, counter electrode, cell body and electrolyte cavity to a reference electrode connector at an outer portion of said cell and forms the means for making electrical contact with said reference electrode.

27. An electrochemical cell for gas detection comprising an impervious nonconductive cell body having an electrolyte cavity and a separate sensor cavity formed therein, said electrolyte cavity being at least partially filled with a liquid electrolyte, said sensor cavity having a plurality of sensor elements stacked therein including a counter electrode positioned at an inner end of said sensor cavity, a gas diffusion sensing electrode containing a catalytic material and positioned at an outer end of said sensor cavity and spaced from said counter electrode, an electrolyte mat positioned between and contacting said counter and sensing electrodes, and a reference electrode disposed within said electrolyte mat and spaced from said counter and sensing electrodes, said reference electrode formed of a non-porous, conductive material coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off the outer end of said sensor cavity and sealing said counter electrode, reference electrode and electrolyte mat within said sensor cavity, said cell including wick means for wicking liquid electrolyte from said electrolyte cavity to said electrolyte mat, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte, with said sensing electrode having a conductive outer surface, said cell including a conductive ring in contact with the outer surface of said sensing electrode and electrically connected to a sensing electrode terminal at an outer portion of said cell, and including a planar sensor contact in contact with said conductive ring and extending to said sensing electrode terminal, said sensor contact having an enlarged portion spaced from and covering said sensing electrode, with said enlarged portion having a plurality of holes therethrough to permit gas flow to said sensing electrode.

28. An electrochemical cell for gas detection comprising an impervious, nonconductive cell body having an electrolyte cavity extending into said cell body from a rear surface thereof and a sensor cavity extending into said cell body from a front surface thereof, a dividing wall separating said sensor cavity and electrolyte cavity, means for closing off said electrolyte cavity at said rear surface, said electrolyte cavity being at least partially filled with a liquid electrolyte, said sensor cavity having a counter electrode at an inner end thereof and adjacent said dividing wall, an electrolyte mat adjacent said counter electrode, a gas diffusion sensing electrode containing a catalytic material and positioned adjacent said electrolyte mat and spaced from said counter electrode, a reference electrode disposed within said electrolyte mat and spaced from said counter and sensing electrodes, with said reference electrode formed of a non-porous, conductive material coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off said sensor cavity at said front surface and sealing said counter electrode, reference electrode and electrolyte mat therein, said cell including a wick which extends between said electrolyte mat and the electrolyte in said electrolyte cavity and passes through said counter electrode and dividing wall, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte, and further including a wire ring positioned behind and in contact with said counter electrode and terminating in a counter electrode lead wire which extends through said dividing wall and through said electrolyte cavity to a counter electrode connector at a rear portion of said cell and forms the means for making electrical contact with said counter electrode.

29. The electrochemical cell of claim 28 further including a reference electrode lead wire connected to said reference electrode and which extends through said electrolyte mat, counter electrode, dividing wall and electrolyte cavity to a reference electrode connector at a rear portion of said cell and forms the means for making electrical contact with said reference electrode.

30. The electrochemical cell of claim 29 wherein said counter electrode connector and said reference electrode connector are carried by a printed circuit board mounted to said cell body at the rear surface.

31. The electrochemical cell of claim 28 wherein said wire ring is formed of platinum.

32. The electrochemical cell of claim 28 further including a carbon cloth positioned behind and in contact with said counter electrode and said wire ring.

33. An electrochemical cell for gas detection comprising an impervious, nonconductive cell body having an electrolyte cavity extending into said cell body from a rear surface thereof and a sensor cavity extending into said cell body from a front surface thereof, a dividing wall separating said sensor cavity and electrolyte cavity, means for closing off said electrolyte cavity at said rear surface, said electrolyte cavity being at least partially filled with a liquid electrolyte, said sensor cavity having a counter electrode at an inner end thereof and adjacent said dividing wall, an electrolyte mat adjacent said counter electrode, a gas diffusion sensing electrode containing a catalytic material and positioned adjacent said electrolyte mat and spaced from said counter electrode, a reference electrode disposed within said electrolyte mat and spaced from said counter and sensing electrodes, with said reference electrode being a metal wire formed into one or more spaced loops coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off said sensor cavity at said front surface and sealing said counter electrode, reference electrode and electrolyte mat therein, said cell including a wick which extends between said electrolyte mat and the electrolyte in said electrolyte cavity and passes through said counter electrode and dividing wall, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte.

34. The electrochemical cell of claim 33 wherein said reference electrode is a platinum wire formed into a plurality of spaced loops and coated with a layer of platinum black.

35. An electrochemical cell for gas detection comprising an impervious, nonconductive cell body having an electrolyte cavity extending into said cell body from a rear surface thereof and a sensor cavity extending into said cell body from a front surface thereof, a dividing wall separating said sensor cavity and electrolyte cavity, means for closing off said electrolyte cavity at said rear surface, said electrolyte cavity being at least partially filled with a liquid electrolyte, said sensor cavity having a counter electrode at an inner end thereof and adjacent said dividing wall, an electrolyte mat adjacent said counter electrode, a gas diffusion sensing electrode containing a catalytic material and positioned adjacent said electrolyte mat and spaced from said counter electrode, a reference electrode disposed within said electrolyte mat and spaced from said counter and sensing electrodes, with said reference electrode formed of a non-porous, conductive material coated with a layer of a catalytic material, and with said counter electrode being a porous, hydrophilic, conductive structure containing a catalytic material, with said catalytic material of said sensing, counter and reference electrodes oxidizing or reducing a particular gas or particular gases coming in contact therewith, said sensing electrode closing off said sensor cavity at said front surface and sealing said counter electrode, reference electrode and electrolyte mat therein, said cell including a wick which extends between said electrolyte mat and the electrolyte in said electrolyte cavity and passes through said counter electrode and dividing wall, and including means for making electrical contact with said counter, reference and sensing electrodes, wherein said counter and reference electrodes are submerged within said sensor cavity by said sensing electrode and any gas contacting said counter and reference electrodes passes through said sensing electrode and is dissolved in said electrolyte, with said sensing electrode having a conductive outer surface, said cell including a conductive ring in contact with the outer surface of said sensing electrode and electrically connected to a sensing electrode terminal at a front portion of said cell, and including a planar sensor contact in contact with said conductive ring and extending to said sensing electrode terminal, said sensor contact having an enlarged portion spaced from and covering said sensing electrode, with said enlarged portion having a plurality of holes therethrough to permit gas flow to said sensing electrode.

* * * * *

UNITED STATES PATENT AND TRADEMARK OFFICE
CERTIFICATE OF CORRECTION

PATENT NO. : 4,769,122

DATED : September 6, 1988

INVENTOR(S) : Carl A. Marrese, David J. D'Amico, Peter M. Noble, Robert L. Novack, John H. Wolf and Andrew A. Sicree It is certified that error appears in the above-identified patent and that said Letters Patent is hereby corrected as shown below:

Under References Cited "Re. 31,914 6/1985 Oswin et al." should read
--Re. 31,914 6/1985 Oswin et al. 204/412--

Column 1 Lines 8-9 "electromechanical" should read --electrochemical--.

Column 3 Line 50 after "and" , first occurrence, insert -- into the electrolyte cavity to wick the electrolyte--.

Column 9 Line 61 "0.040' " should read --.040"--.

Column 10 Line 32 "and" (second occurrence) should read --the--.

Claim 21 Column 13 Line 56 after "of" insert --a--.

Claim 24 Column 14 Line 50 "electrode" (first occurrence) should read --electrodes--.

Signed and Sealed this

Sixth Day of June, 1989

Attest:

DONALD J. QUIGG

Attesting Officer

Commissioner of Patents and Trademarks